United States Patent [19]

Otake

[11] Patent Number: 5,947,897
[45] Date of Patent: Sep. 7, 1999

[54] MEDICAL ELECTRODE ASSEMBLY AND MEDICAL EQUIPMENT PROVIDED WITH THE MEDICAL ELECTRODE ASSEMBLY

[76] Inventor: Tsutomu Otake, 3-60-1, Yotsuya-Cyou, Aichi-ken, Toyokawa-shi, Japan, 422

[21] Appl. No.: 08/752,625

[22] Filed: Nov. 19, 1996

[30] Foreign Application Priority Data

Dec. 28, 1995 [JP] Japan .................................. 7-352679

[51] Int. Cl.⁶ .................................................. A61N 1/08
[52] U.S. Cl. ...................... 600/372; 600/509; 600/522; 607/115; 607/152; 607/46; 128/898
[58] Field of Search ..................... 128/639–641, 128/644, 696, 702–704, 734; 607/46, 74, 115, 148, 149, 152; 600/301, 372, 382, 386, 388, 389, 509, 522

[56] References Cited

U.S. PATENT DOCUMENTS

| | | | |
|---|---|---|---|
| 4,055,190 | 10/1977 | Tany ........................................... | 607/46 |
| 4,115,864 | 9/1978 | Vick et al. . | |
| 4,408,617 | 10/1983 | Auguste ..................................... | 607/59 |
| 4,532,930 | 8/1985 | Crosby et al. ............................. | 607/57 |
| 4,577,639 | 3/1986 | Simen et al. .............................. | 128/696 |
| 5,012,816 | 5/1991 | Lederer . | |
| 5,042,498 | 8/1991 | Dukes ........................................ | 128/696 |
| 5,184,620 | 2/1993 | Cudahy et al. ........................... | 128/696 |
| 5,483,967 | 1/1996 | Ohtake . | |
| 5,564,429 | 10/1996 | Bornn et al. .............................. | 128/644 |

FOREIGN PATENT DOCUMENTS 0 538 739 A1 10/1992 European Pat. Off. .

OTHER PUBLICATIONS

Patent Abstracts of Japan, vol. 16, No. 128 (C–0924), Apr. 2, 1992 & JP 03 292959 A (Aika K.K.), Dec. 24, 1991, *Abstract*.

IBM Technical Disclosure Bulletin, vol. 23, No. 7B, Dec. 1980, New York, (US), pp. 3493–3497, XP002029529, C. W. Coker et al.: "EKG Artifact Rejection Circuit" *the whole document*.

*Primary Examiner*—Jack W. Lavinder
*Assistant Examiner*—David M. Ruddy
*Attorney, Agent, or Firm*—Nixon & Vanderhye P.C.

[57] ABSTRACT

A electrocardiographic electrode assembly is attached on a spot of the body that is roughly inside an electrocardiowave-appearing region, and an optimum signal discriminating circuit of an electrocardiograph discriminates an electrode that is most suitable for an electrocardiographic measurement out of the plural electrodes of the electrocardiographic electrode assembly. The electrocardiograph receives electric signals (electrocardiowaves) captured by the discriminated electrode, and stores the electric signals in a memory. The electric signals stored in the memory, after a measurement of the electrocardiovaves finishes, is given as an electrocardiographic pattern to a doctor for diagnosis. In this manner, in the electrocardiographic measurement, the electrocardiographic electrode assembly is only needed to be attached on a spot of the body that is roughly inside the electrocardiovave-appearing region. Therefore, even an amateur or nonexpert can easily perform an electrocardiographic measurement.

22 Claims, 8 Drawing Sheets

MEDICAL ELECTRODE ASSEMBLY AND MEDICAL EQUIPMENT PROVIDED WITH THE MEDICAL ELECTRODE ASSEMBLY

BACKGROUND OF THE INVENTION

1. Field of the Invention

The present invention relates to a medical electrode assembly for capturing electrocardiowaves appearing on a surface of a human body and stimulating acupuncture points on the body to give a medical treatment, and a medical device provided with the medical electrode assembly.

2. Description of Related Art

When a diagnosis of a heart is done using an electrocardiograph, an electrode for an electrocardiographic measurement is attached on a region (hereinafter, electrocardiowave-appearing region) where specific electrocardiowaves appear on a surface of a human body, and the electrocardiowaves are captured by the electrode. The captured electrocardiowaves are given by an electrocardiograph as an electrocardiographic pattern to be presented to a doctor. The doctor diagnoses the state of the heart on the basis of the electrocardiographic pattern.

However, the electrode for electrocardiographic measurement is very difficult to attach correctly, and if an amateur or nonexpert attaches such an electrode, the person is apt to attach the electrode on a position off the electrocardiowave-appearing region. When the electrode is attached to a position off the electrocardiowave-appearing region, a desired electrocardiogram cannot be attained and undesired noises are captured to mislead the diagnosis by the doctor. In this situation, the subject has to visit the hospital even when the subject only wants to attach the electrode of a portable type electrocardiograph, although, naturally, the subject visits to seek the doctor's diagnosis. It is conceivable to widen the area of the electrode so that the electrode can cover the electrocardiowave-appearing region even when the electrode is set somewhat off the attachment position. However, widening the area of the electrode captures not only the desired elecrocardiowaves, but also noises as well, which also misleads the diagnosis by the doctor.

When using a medical device such as a low frequency therapy equipment that gives electric signals to the body of a subject to perform a medical treatment, an electrode for giving medical electric signals is attached to a region (acupuncture point region) containing acupuncture points and the peripheral region thereof that can feel the electric signals given to the region as stimuli to the acupuncture points. Applying medical electric signals such as a low frequency current to the attached electrode gives stimuli to the acupuncture points to produce a good medical effect.

However, the electrode for medical treatment is very difficult to attach correctly, and if an amateur or nonexpert attaches such an electrode, the person is apt to attach the electrode on a position off the acupuncture region. If the electrode is attached to a position off the acupuncture region and a low frequency current is applied to the electrode, the medical effect will remarkably reduce. When, even if an expert attaches the electrode precisely to the acupuncture region, the medical electric signals are applied for a long time continuously to one point of the acupuncture region, habituation in the acupuncture points against the stimuli will be created as the time passes by the electric signals and the medical effect will be reduced.

SUMMARY OF THE INVENTION

The present invention has been made in view of the foregoing problems, and an object of the invention is to provide a medical device that can operate normally even when an amateur or nonexpert attaches a medical electrode assembly to the body of a subject, and the medical electrode assembly that is used in connection with the medical device.

The medical device according to the first aspect of the present invention is provided with a medical electrode assembly attached on a surface of the body of a subject and a measuring unit connected to the medical electrode assembly. The medical electrode assembly has a plurality of electrodes electrically isolated from each other. The measuring unit, on the other hand, is provided with an electrode detection device for detecting an electrode suitable for measurement out of the plural electrodes of the medical electrode assembly, and a storage device for storing a measurement result measured by an electrode detected by the electrode detection device.

In the foregoing medical device, when an operator attaches the medical electrode assembly on a spot on the surface of the body that is roughly suitable for measurement, the electrode detection device of the measuring unit detects an electrode suitable for measurement out of the plural electrodes of the medical electrode assembly. When an electrode suitable for measurement is detected, a measurement result measured using the electrode is stored by the storage device for use in a diagnosis by a doctor. Thus, in the medical device according to the first aspect of the invention, the operator only needs to attach the medical electrode assembly on a spot on the surface of the body that is roughly suitable for measurement; and therefore, an amateur or nonexpert can easily make an accurate measurement.

The medical device according to the second aspect of the present invention is provided with a medical electrode assembly attached on a surface of the body of a subject and a curing unit connected to the medical electrode assembly. The medical electrode assembly has a plurality of electrodes electrically isolated from each other. The curing unit, on the other hand, is provided with an electrode detection device for detecting an electrode suitable for curing out of the plural electrodes of the medical electrode assembly, and a curing device for curing by using an electrode detected by the electrode detection device.

In the medical device according to the second aspect of the invention, when an operator attaches the medical electrode assembly on a spot on the surface of the body that is roughly suitable for curing, the electrode detection device of the curing unit detects an electrode suitable for curing out of the plural electrodes of the medical electrode assembly. When an electrode suitable for curing is detected, the curing device proceeds a curing using the detected electrode. Thus, in the medical device according to the second aspect of the invention, the operator only needs to attach the medical electrode assembly on a spot on the surface of the body that is roughly suitable for curing; and therefore, an amateur or nonexpert can easily make an effective curing.

BRIEF DESCRIPTION OF THE DRAWINGS

Preferred embodiments of the present invention will be described in detail with reference to the following drawings wherein.

DETAILED DESCRIPTION OF THE PREFERRED EMBODIMENTS

Figure 1:
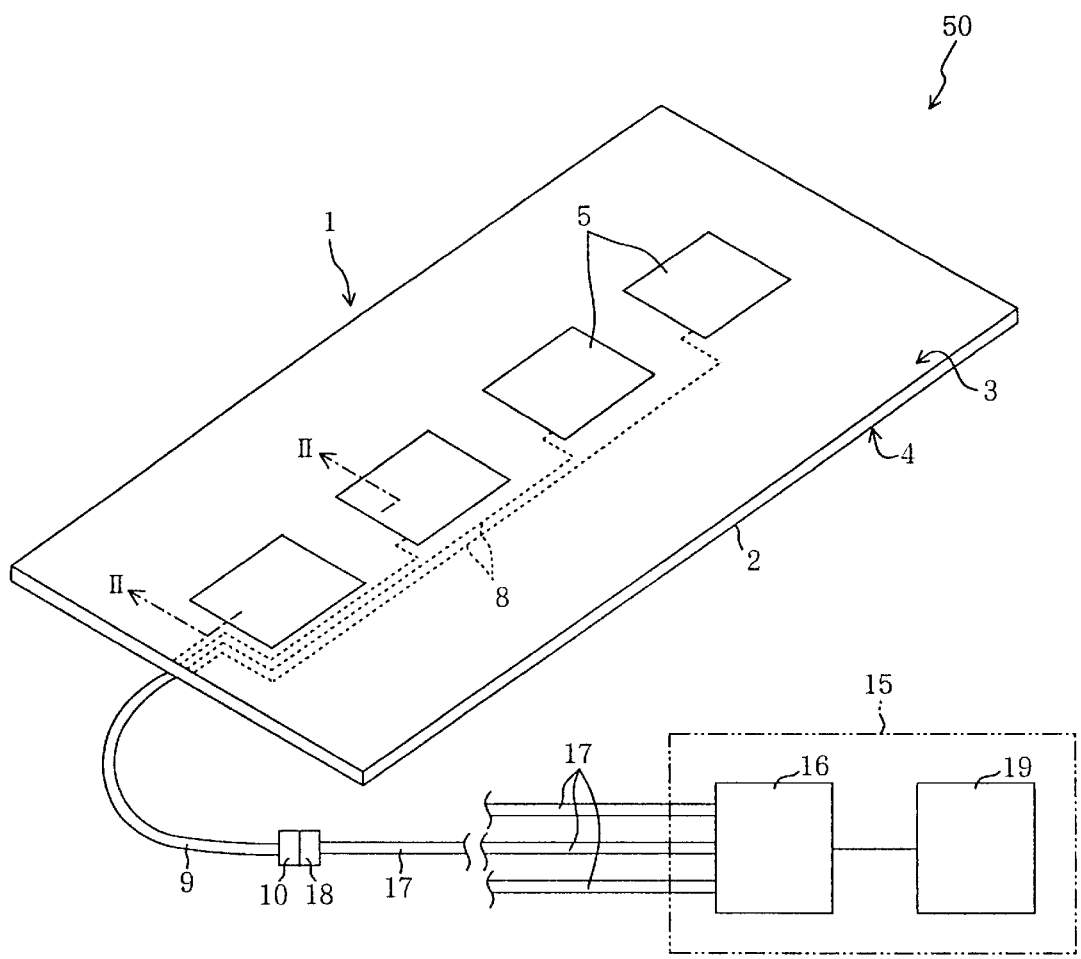
FIG. 1 is a schematic perspective view of an electrocardiographic measurement unit in the first embodiment.
Figure 2:
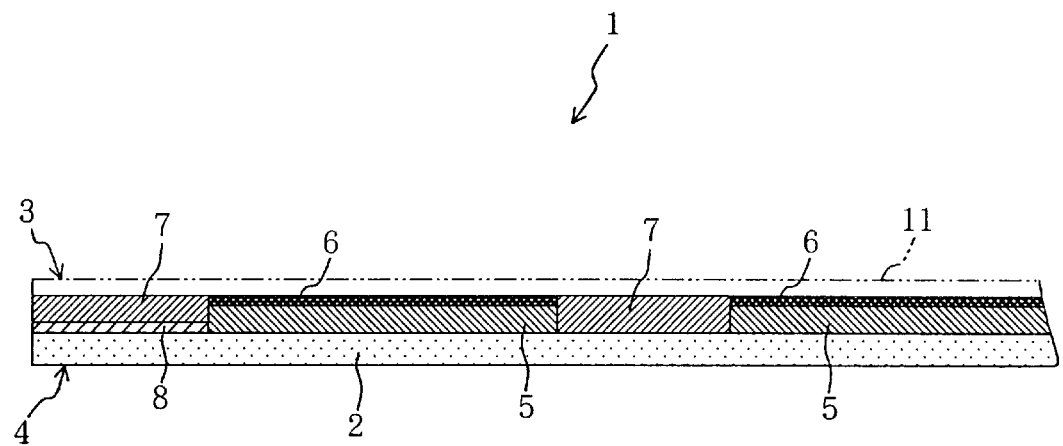
FIG. 2 is a sectional side elevation taken along the line II—II in FIG. 1.

The first embodiment of the present invention will hereafter be described with reference to the drawings. In FIG. 1, an electrocardiographic measurement unit 50 is shown as one example of a medical device provided with a medical electrode assembly. This electrocardiographic measurement unit 50 is constructed such that an electrocardiographic electrode assembly 1 is connected to an electrocardiograph 15 by a connector 10 and 18. The electrocardiographic electrode assembly 1 captures electrocardiowaves appearing on the skin of a subject body, and the electrocardiograph 15 stores the electrocardiowaves captured by the electrocardiographic electrode assembly 1. FIG. 2 is a sectional side elevation taken along the line II—II in FIG. 1, namely, a partial side section of the electrocardiographic electrode assembly 1. Referring to FIG. 1 and 2, the electrocardiographic electrode assembly 1 will now be described. In FIG. 1 and 2, an upper side 3 of the electrocardiographic electrode assembly 1 is the body side (inner surface) when the electrocardiographic electrode assembly 1 is attached to a human body, and a lower side 4 is the opposite side (outer surface).

The electrocardiographic electrode assembly 1 is composed of a plurality of electrodes 5 made of conductive metal plates which are attached on the upper side 3 of a base material 2 by glue. The base material 2 supports the plural electrodes 5 and is formed in a strip of tape having a sufficient length to support the plural electrodes 5. The base material 2 is preferably provided with flexibility whereby it is easily deformed in compliance with irregularities of the subject body so as to easily fit to the skin of the body, insulation capability to hold the plural electrodes 5 isolated from each other, waterproof capability for waterproofing the plural electrodes 5, and electric shielding capability for preventing electric noises from coming through into the plural electrodes 5. To meet the foregoing requirements, the base material 2 of this embodiment is formed of a soft sheet material of a synthetic resin in which a conductive film is incorporated. Furthermore, there is a wider space between the edge of the base material 2 and the edges of the electrodes 5 so that the base material 2 having waterproof capability can completely seal the electrodes 5 when attaching the electrocardiographic electrode assembly 1 on the body. The base material 2 may be formed of a material that lacks in a part of the foregoing four properties depending on the environments of usage.

The electrodes 5 capture electric signals (electrocardiowaves) from a surface of the body where the electrodes 5 are attached. In this embodiment, the electrodes 5 are attached on the upper side 3 of the base material 2 by glue, however, the electrodes 5 may be formed such that a conductive foil is made on the upper side 3 of the base material 2 by means of the printed circuit board technique. The size of each of the electrodes 5 is preferably sufficient to capture electrocardiowaves with a necessary articulation when the electrodes 5 are attached on a desired electrocardiowave-appearing region. In this embodiment, each electrode 5 is a square having a side of some mm to about 1 cm. Here, the term "articulation" is defined as a ratio of desired electrocardiowaves against the other noises which are both captured by the electrodes 5; and "necessary articulation" is an articulation such that the characteristics of an electrocardiogram from captured electric signals is recognized to be usable for a diagnosis. The shape of the electrodes 5 is not necessarily a square, and it may be a round shape or other shapes.

The space between any two of the electrodes 5 is specified as a minute space such that the electrodes do not electrically come into contact with each other. Thus, when the electrocardiographic electrode assembly 1 is attached on a surface of the body, even if one of the electrodes 5 is attached to a spot deviated from an electrocardiowave-appearing region (and consequently it cannot capture electrocardiowaves with the necessary articulation), the other electrodes 5 are attached to the electrocardiowave-appearing region without deviation (or, if the other electrodes 5 are attached to a slightly deviated position from the electrocardiowave-appearing region). Thereby, the electrocardiowaves are designed to be captured with the necessary articulation. Furthermore, the space between any two of the electrodes 5 is constructed such that the distance between centers of adjacent electrodes 5 is at most less than the width of the electrocardiowave-appearing region.

Layers of conductive pastes 6 are provided on the upper surface of each of the electrodes 5, which reduce a contact resistance between the surface of a skin on which the electrocardiographic electrode assembly 1 is attached and the electrodes 5. Signal conductors 8 connected to the electrodes 5 are printed on the upper surface of the base material 2 by the printed circuit board technique. The signal conductors 8 transmit electric signals (electrocardiowaves) captured by the electrodes 5 to an electrocardiograph 15 through a cable 9, which have the same number of signal conductors as the number of the electrodes 5. Each of the signal conductors 8 is connected to each of the electrodes 5 one to one. Any one of the signal conductors 8 is isolated from the other signal conductors and from the other electrodes except one electrode to which the signal conductor is connected. Furthermore, adhesives 7 are provided except where the electrodes 5 are on the upper surface of the base material 2, which stick the electrocardiographic electrode assembly 1 onto the skin surface. The adhesives 7 have insulation capability to isolate each of the electrodes 5. Moreover, the adhesives 7 and the base material 2 sandwich the foregoing signal conductors 8 therebetween to isolate the signal conductors 8.

A protective sheet 11 covers the upper surface 3 of the conductive pastes 6 and the adhesives 7. This protective sheet 11 prevents the conductive pastes 6 and the adhesives 7 from sticking to other parts before using the electrocardiographic electrode assembly 1, namely, before attaching the electrocardiographic electrode assembly 1 on a body, or to prevent dust and the like from sticking to the conductive pastes 6 and the adhesives 7. Accordingly, the protective sheet 11 is stripped off from the upper surface of the conductive pastes 6 and the adhesives 7 when using the electrocardiographic electrode assembly 1, and it is made of a sheet material that is easy to be stripped off.

The electrocardiographic electrode assembly 1 thus constructed is connected to the electrocardiograph 15 through the cable 9 and a cable 17. A flexible multicore cable is used for the cable 9, and each of the core conductors is separately connected to each of the signal conductors 8. The other end of the cable 9 is attached to a multiconnector 10, and the multiconnector 10 connects with a multiconnector 18 of the electrocardiograph 15. The multiconnector 18 of the electrocardiograph 15 connects with the flexible multicore cable 17, and the other end of the cable 17 is connected to the electrocardiograph 15. Thus, each of the electric signals (electrocardiowaves) captured by each of the electrodes of the electrocardiographic electrode assembly 1 can individually enter the electrocardiograph 15.

The electrocardiograph 15 includes a Holter electrocardiograph (portable electrocardiograph) that a subject 20 can carry, and a stationary type electrocardiograph that is fixed in a hospital or the like. The electrocardiograph 15 is provided with an optimum signal discriminating circuit 16 and a memory 19. The optimum signal discriminating circuit 16 is a circuit for discriminating the electrode 5 that captures the optimum electric signal (electrocardiowave) among the electric signals captured by the electrodes 5 of the electrocardiographic electrode assembly 1. The optimum signal discriminating circuit 16 stores a standard electrocardiographic pattern (sample signal), compares each of electric signals captured by the electrodes 5 with the standard pattern, and discriminates an electrode that captures the optimum electric signal. The memory 19 is a circuit to store electric signals (electrocardiowaves) given by an electrode 5 discriminated by the optimum signal discriminating circuit 16. The memory 19 is constructed by a RAM, flash memory, magnetic disc, and magnetic tape and the like in the portable Holter electrocardiograph. In the stationary type electrocardiograph, on the other hand, the memory 19 is constructed by, in addition to the foregoing storage devices, a display unit such as an LCD or CRT, and a pen recorder.

Figure 3:
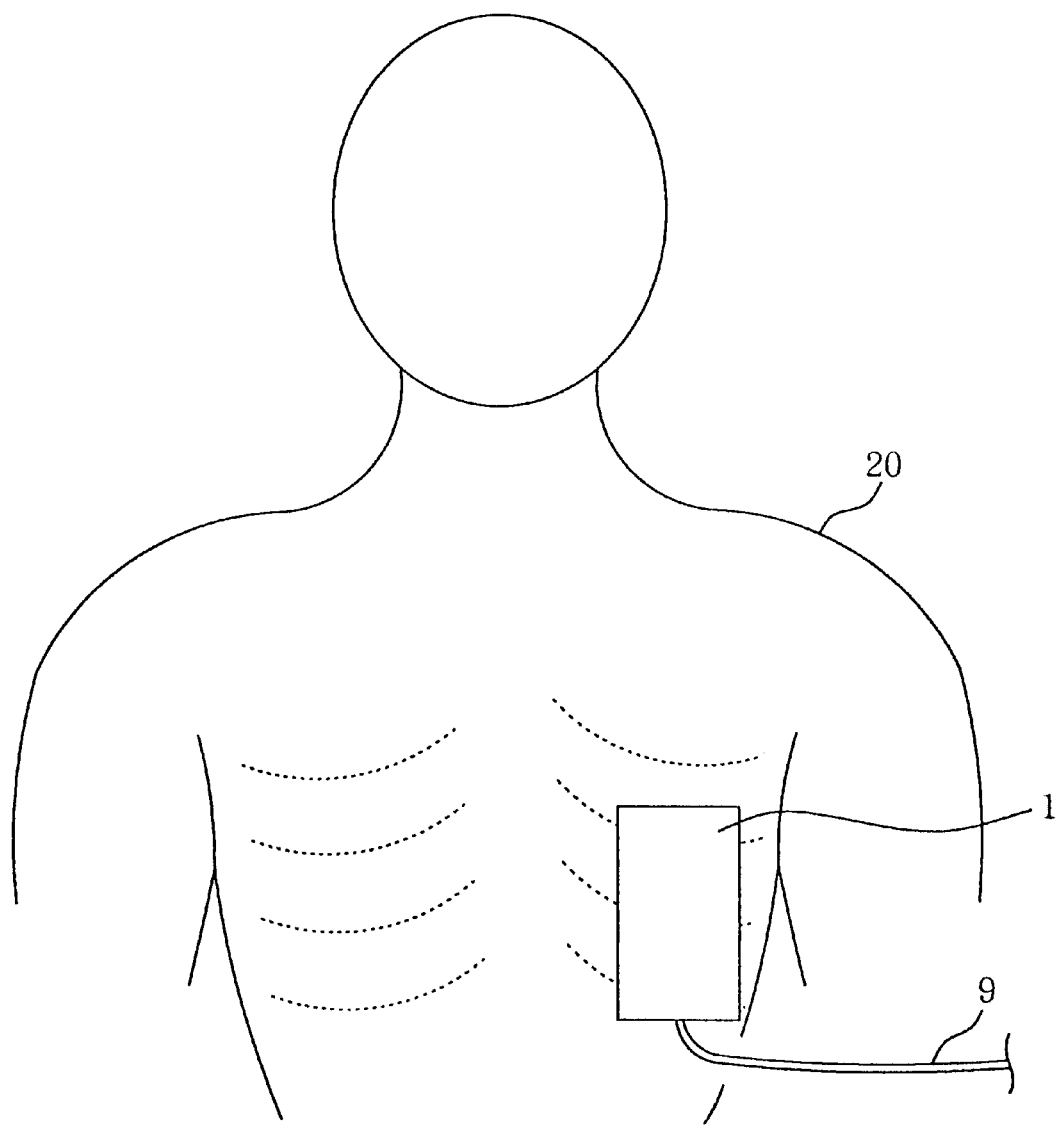
FIG. 3 is an illustration showing a state in which an electrocardiographic electrode assembly is attached.

FIG. 3 illustrates an electrocardiographic measurement unit 50 in use. When an electrocardiographic measurement is performed, first, the protective sheet 11 is stripped off. As shown in FIG. 3, the electrocardiographic electrode assembly 1 is attached on a surface of the body of the subject 20, on a spot that is roughly inside the electrocardiowave-appearing region, so as to face the conductive pastes 6 and adhesives 7 to the body. Then, the electrocardiographic electrode assembly 1 is applied on the body of the subject 20 and held by the adhesive force of the adhesives 7. The electrocardiographic electrode assembly 1 is only needed to be attached on a spot on the surface of the body of the subject 20 that is roughly inside the electrocardiowave-appearing region; and therefore, an amateur or nonexpert cannot make a mistake in finding a good spot to attach.

Figure 4:
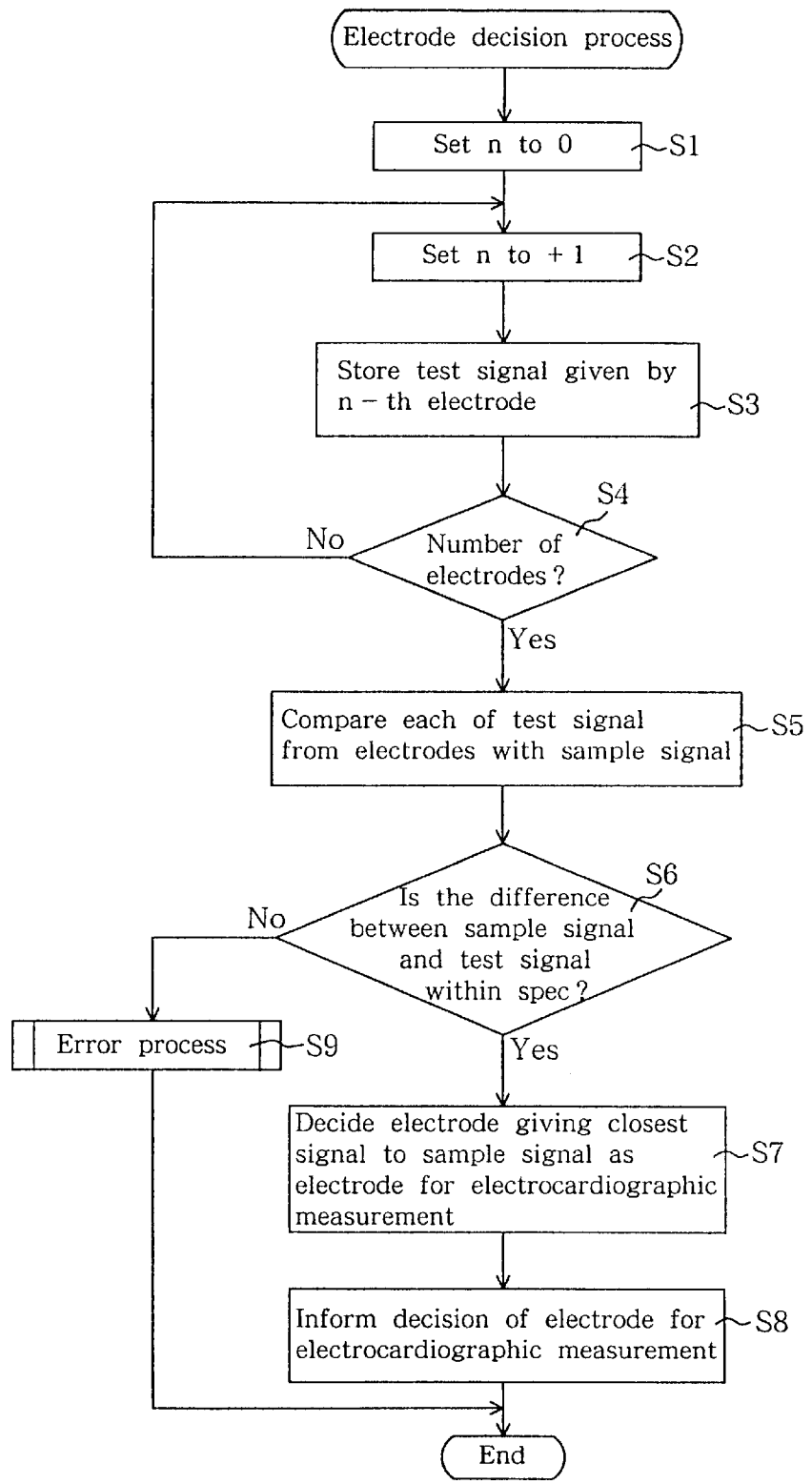
FIG. 4 is a flow chart for an electrode decision process in the first embodiment.

FIG. 4 is a flow chart showing an electrode decision process. This process discriminates an electrode 5 that captures the optimum electric signals (electrocardiowaves) from among the plural electrodes 5 of the electrocardiographic electrode assembly 1 attached on the body of the subject 20, and decides the electrode 5 as the electrode for electrocardiographic measurement of the subject 20. This process is performed by the optimum signal discriminating circuit 16.

First, in the electrode decision process, the value of the variable n representing the number of the electrode 5 is set to "0" (S1). Next, the value of n is set to "+1" (S2), and an electric signal (electrocardiowave) sent out by the n-th electrode 5 is stored in a memory of the optimum signal discriminating circuit 16 as a test signal (S3). The foregoing process S2 and S3 are performed to all the electrodes 5 of the electrocardiographic electrode assembly 1. Therefore, the judgment is done as to whether or not the value of n coincides with the number of the electrodes 5 of the electrocardiographic electrode assembly 1 (S4); if the judgment is no (S4: No), the process returns to S2.

On the other hand, if the value of n coincides with the number of the electrodes 5 of the electrocardiographic electrode assembly 1 (S4: Yes), the process of S2 and S3 are all complete. Therefore, in this case, the test signals of the electrodes 5 stored in the process S3 are compared with a standard electrocardiographic pattern (sample signal) stored beforehand in the optimum signal discriminating circuit 16 (S5). On the basis of the comparison, if the difference between the sample signal and any of the test signals is within a specified range (S6: Yes), an electrode 5 that gave a test signal closest to the sample signal among the test signals within the specified range is decided as the electrode for the electrocardiographic measurement (S7). The selected electrode 5 can be judged as an electrode attached in the electrocardiowave-appearing region. When the electrode for the electrocardiographic measurement is decided (S7), the operator is informed of the decision (S8). For this purpose, the electrocardiograph 15 makes a normal buzzing sound, or emits a normal lighting. On the other hand, if the comparison result shows that the difference between the sample signal and any of the test signals is not within the specified range (S6: No), all of the electrodes 5 are judged to be attached on spots outside of the electrocardiowave-appearing region. In this case, an error process is performed to inform that the electrocardiographic measurement is impossible (S9). In this error process (S9), the electrocardiograph 15 makes an abnormal sound for informing an error, or emits an abnormal lighting for informing an error.

When the electrode 5 for the electrocardiographic measurement is decided (S7), the electrode decision process is completed. Afterward, the electric signals captured by the selected electrode 5 are stored in the memory 19. After completing the measurement, the electric signals (electrocardiowaves) stored in the memory 19 are fed from the electrocardiograph 15 and presented to a doctor for the diagnosis.

The electrode decision process as shown in FIG. 4 is performed not only at the beginning of the electrocardiographic measurement, but also in a periodic interval. Therefore, when the subject removes the electrocardiographic electrode assembly 1 from the body during the measurement and again attaches it on the body, the electrode 5 for the electrocardiographic measurement is designed to be decided again; and in such a case, the electrocardiowaves can be accurately measured. The electrocardiograph 15 may alternatively or additionally be provided with a reset button so that the electrode decision process can be performed when this reset button is pressed. With this construction, even when the subject changes the attachment of the electrocardiographic electrode assembly 1, the most appropriate electrode 5 for the electrocardiographic measurement is decided whenever the subject presses the reset button, leading to the measurement of appropriate electrocardiowaves. The electrode decision process may yet alternatively be designed to be performed when detecting a change of the attachment of the electrocardiographic electrode assembly 1 from a change of the electrostatic capacity of the electrocardiographic electrode assembly 1, as the electrostatic capacity changes when the electrocardiographic electrode assembly 1 is removed from the body.

Thus, according to the electrocardiographic measurement unit 50 of this embodiment, the electrocardiographic electrode assembly 1 is only needed to be attached on a spot on the body that is roughly inside the electrocardiowave-appearing region, so that an electrode 5 suitable for the electrocardiographic measurement will automatically be discriminated, and the electrocardiowaves captured by the electrode 5 are stored in the memory 19. Therefore, a nonexpert or amateur can easily measure electrocardiowaves.

This means that a subject him or herself can attach the electrocardiographic electrode assembly 1 correctly on his or her body. Therefore, in case of a portable electrocardiograph, the electrocardiograph can be mailed to the subject, which means that the subject does not have to visit the hospital when the electrocardiographic electrode assembly 1 is attached, and the subject needs to visit the hospital only when the subject is informed of the diagnosis of the measurement result. While previously the subject has been visiting the hospital twice for one electrocardiographic measurement, by virtue of the invention, the subject only needs to visit once, which greatly reduces a burden of the subject.

Figure 5:
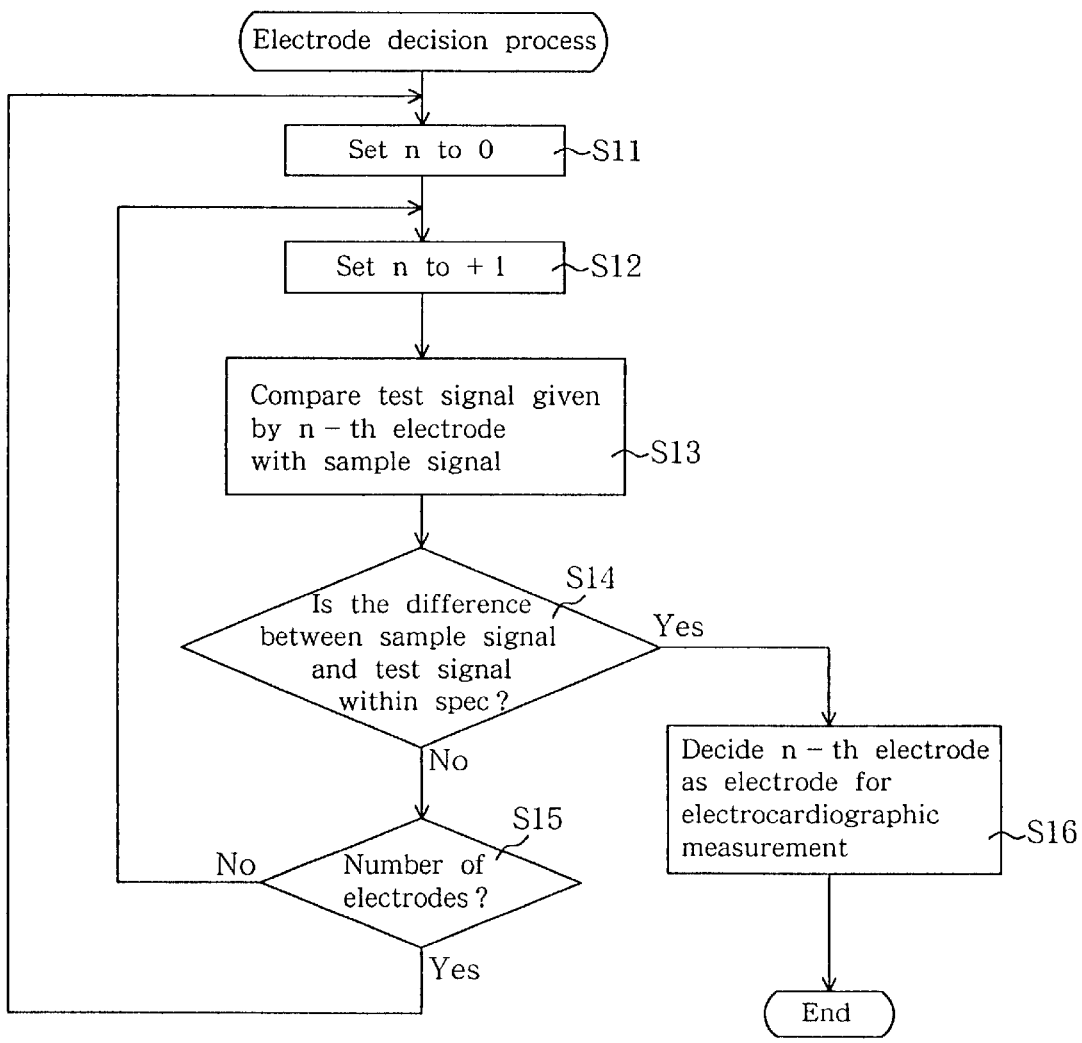
FIG. 5 is a flow chart for an electrode decision process in the second embodiment.

Next, the second embodiment will be described with reference to FIG. 5. The second embodiment is constructed such that the electrode decision process (FIG. 4) of the first embodiment is modified. The electrocardiographic measurement unit 50 is constructed in the same manner as that in the first embodiment. The same parts as in the first embodiment are given the same numbers, and only the different parts from the first will be described.

First, in the electrode decision process, the value of the variable n representing the number of the electrode 5 is set to "0" (S11). Next, the value of n is set to "+1" (S12), and an electric signal (test signal) sent out by the n-th electrode 5 is compared with a standard electrocardiographic pattern (sample signal) stored beforehand in the optimum signal discriminating circuit 16 (S13). From the comparison result, if the difference between the test signal and the sample signal is not within a specified range (S14: No), the value of n is updated and the next electrode 5 is selected. The judgment is done to determine whether or not the value of n coincides with the number of the electrodes 5 (S15). If the judgment is no (S15: No), the process returns to S12 to select the next electrode 5. If the judgment is yes (S15: Yes), the process returns to S11 to return to the first electrode 5 again.

On the other hand, from the comparison result (S13), if the difference between the test signal and the sample signal is within the specified range (S14: Yes), the n-th electrode 5 is decided as an electrode for the electrocardiographic measurement (S16), and this process ends. Because the electrode 5 gave a test signal of which difference from the sample signal was within the specified range, the electrode 5 can be judged as an electrode attached in the electrocardiowave-appearing region.

In the electrode decision process of the first embodiment (FIG. 4), test signals from all the electrodes are extracted first, and afterward, an electrode 5 that captured an optimum test signal was decided as the electrode for the electrocardiographic measurement. In the electrode decision process of the second embodiment (FIG. 5), when an electrode 5 giving the test signal within the specified range is detected even before other test signals are extracted from the other electrodes 5, the electrode 5 is decided as the electrode for the electrocardiographic measurement (S16). Therefore, the electrode decision process can be completed in a shorter time when the electrocardiographic electrode assembly 1 having multiple electrodes 5 is used.

Figure 6:
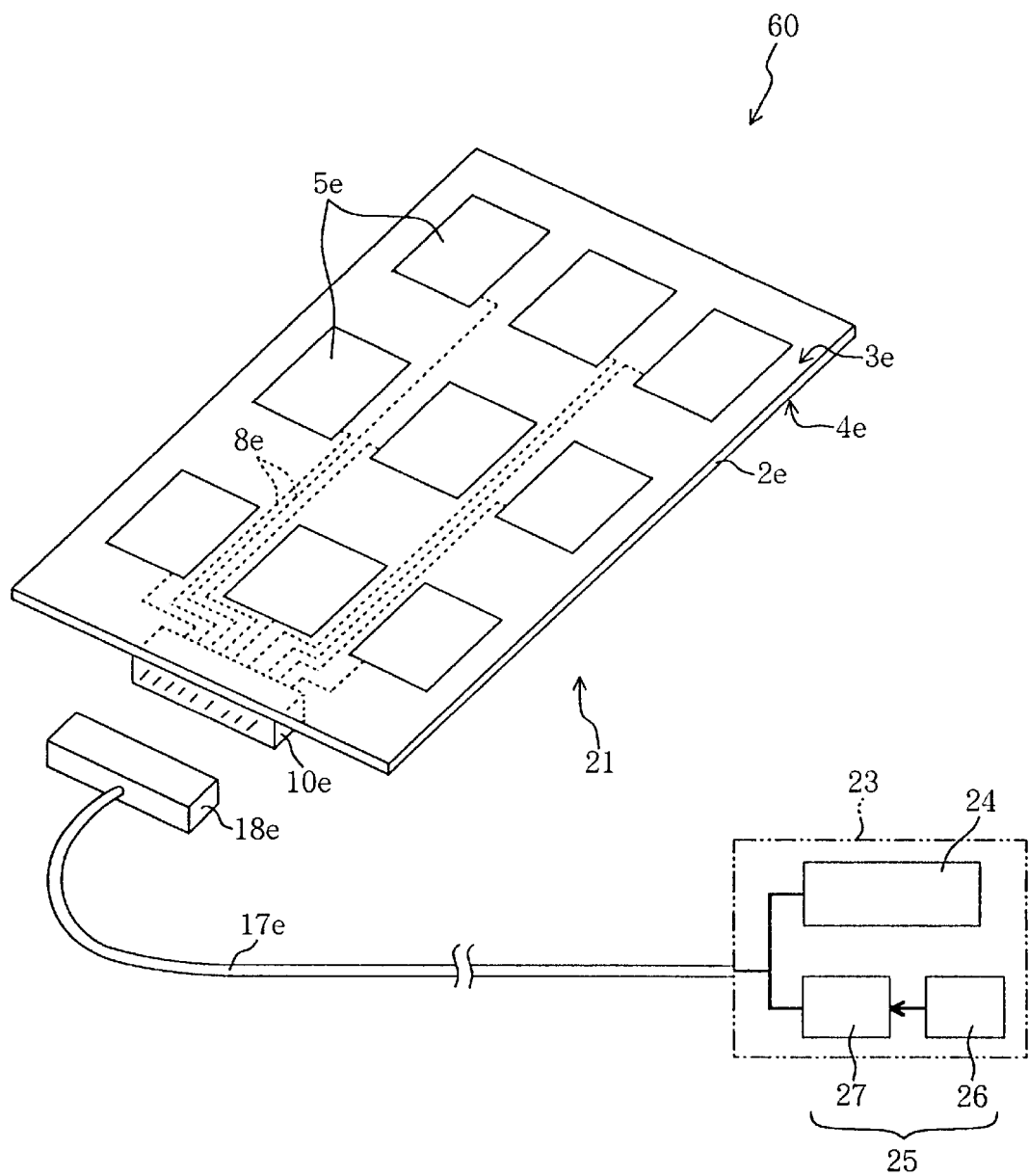
FIG. 6 is a schematic perspective view of a low frequency curing unit in the third embodiment.

Next, the third embodiment will be described with reference to FIG. 6. In the third embodiment, a low frequency curing unit 60 is illustrated as another example of a medical equipment provided with an electrocardiographic electrode assembly. The low frequency curing unit 60 flows a low frequency current from the skin of a human body to perform a curing, and it is constructed such that a low frequency curing electrode assembly 21 is coupled to a low frequency current generator 23 by a connector 10e and 18e. The parts composed of members identical to the first embodiment, of the low frequency curing unit 60 of the third embodiment, are given the same number with appended reference letter "e", and a repetitive description will be omitted.

The low frequency curing electrode assembly 21 is provided with nine electrodes 5e in total with three longitudinal and three lateral. One of these electrodes 5e is connected to the positive terminal of the low frequency current generator 23 and another 5e to the negative terminal so that a low frequency curing can be done. The space between any two of the electrodes 5e is specified as a minute space such that the electrodes do not electrically come into contact with each other. Thus, when the low frequency curing electrode assembly 21 is attached on a skin surface of the body, even if one of the electrodes 5e is attached to a spot deviated from an acupuncture point region (and consequently it cannot stimulate an acupuncture point), the other electrodes 5e are attached to the acupuncture region without deviation to be able to give stimuli to the acupuncture point. Furthermore, the space between any two of the electrodes 5e is constructed such that the distance between centers of adjacent electrodes 5e is at most less than the width of the acupuncture point region.

Thus, the low frequency curing electrode assembly 21 is constructed such that, in the electrocardiographic electrode assembly 1 of the first embodiment, the number of the electrodes are increased, the cable 9 is removed, and the connector 10 is directly attached to the base material 2. Adhesives are applied on the upper side 3e of a base material 2e of the low frequency curing electrode assembly 21, and conductive pastes are applied on the upper side 3e of the electrodes 5e. Signal conductors 8e are provided to the electrodes 5e, one to one. Furthermore, a protective sheet covers the upper side 3e of the low frequency curing electrode assembly 21 before it is used, and the protective sheet is designed to be stripped off when the assembly 21 is used.

The low frequency current generator 23 is provided with an optimum electrode discriminating circuit 24 and signal supply circuit 25. The optimum electrode discriminating circuit 24 discriminates an electrode attached in the acupuncture point region, among the plural electrodes 5e of the low frequency curing electrode assembly 21 attached on a human body. The optimum electrode discriminating circuit 24 measures each electric conductivity (resistance) of the electrodes 5e, and discriminates one electrode 5e having the highest electric conductivity (lowest resistance) as an electrode that is attached in the acupuncture point. The signal supply circuit 25 supplies a low frequency current alternately to the electrode 5e discriminated by the optimum electrode discriminating circuit 24 and electrodes 5e adjacent the foregoing electrode 5e. The signal supply circuit 25 comprises a signal generator 26 for generating a low frequency current and a switching circuit 27 for switching electrodes to apply the low frequency current.

Next, the usage of the low frequency curing unit 60 will be described. First, the protective sheet of the low frequency curing electrode assembly 21 is stripped off. The low frequency curing electrode assembly 21 is attached on a surface of the body of a subject, on a spot that is roughly inside the acupuncture point region where a curing is needed, so as to face the conductive pastes and adhesives to the body. Then, the low frequency curing electrode assembly 21 is applied on the body of the subject and held by the adhesives.

Figure 7:
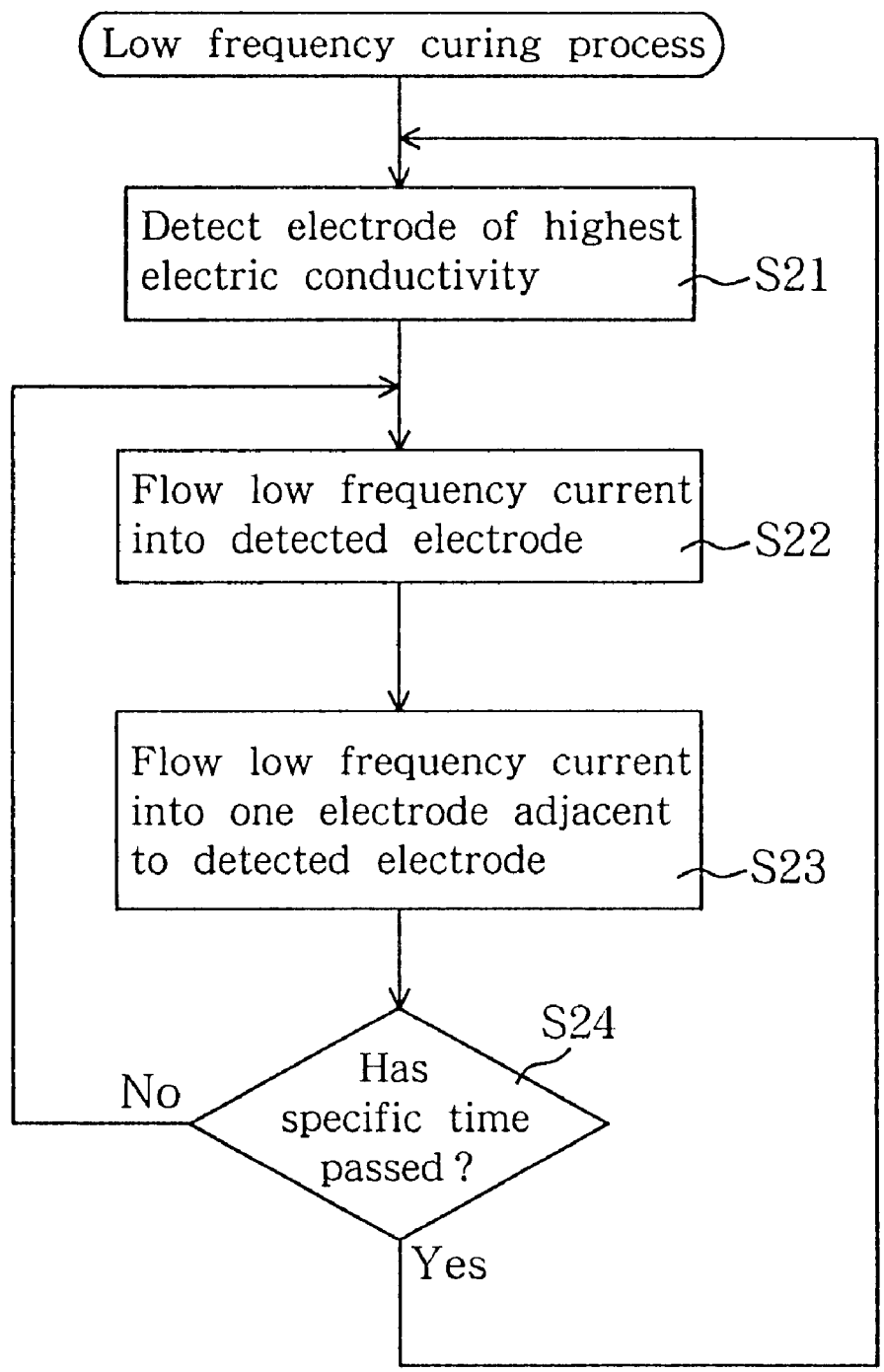
FIG. 7 is a flow chart of the low frequency curing process in the third embodiment.

FIG. 7 is a flow chart illustrating a low frequency curing process. This process is executed in the low frequency current generator 23, after the low frequency curing electrode assembly 21 is applied on the subject body. In the low frequency curing process, the optimum electrode discriminating circuit 24 detects one electrode 5e having the highest electric conductivity out of the electrodes 5e of the low frequency curing electrode assembly 21 (S21). The optimum electrode discriminating circuit 24 measures the electric conductivity of the electrodes 5e, after measuring of all the electrodes 5e, compares each electric conductivity of the electrodes 5e, and detects one electrode 5e having the highest electric conductivity.

The detected electrode 5e can be judged as an electrode attached inside an acupuncture point region. Accordingly, a signal supply circuit 25 flows a low frequency current generated by the signal generator 26 into the foregoing electrode 5e (S22). One electrode adjacent to the detected electrode 5e is used as the negative terminal. Next, the switching circuit 27 stops applying the low frequency current to the detected electrode 5e, and flows the low frequency current into one of the electrodes 5e adjacent to the detected electrode 5e (S23). Steps S22 and S23 are repeated until a specific time passes (S24: No). A low frequency current flows alternately into the electrode 5e detected by the process S21 and the electrode 5e close thereto. When a low frequency flows into one acupuncture point continuously, however, there occurs habituation on the acupuncture point, which reduces the curing effect by half. In this embodiment, however, switching the flow path of the low frequency current from the electrode 5e detected by the process S21 to another electrode 5e surrounding the detected electrode 5e alternately can prevent the habituation of the acupuncture point so as not to reduce the curing effect by half. The electrode 5e where a low frequency current is run by step S23 is changed on each predetermined timing by the switching circuit 27.

When steps S22 and S23 are repeated for the specific time (S24: Yes), the process returns to step S21, again an electrode 5e giving the highest electric conductivity is detected, and the foregoing steps S22–S24 are repeated. Continuing the low frequency curing for the specific time (S22, S23) will remove a pain on the spot where the curing is applied. In consequence, a pain will appear on a spot where the curing is not applied. Therefore, the process S21 is executed in order to change the curing spot for every specific time.

Thus, according to the low frequency curing unit 60 of the third embodiment, the low frequency curing electrode assembly 21 is only needed to be attached on a spot on the body that is roughly inside the acupuncture point region, so that an electrode 5e attached in the acupuncture point region will automatically be discriminated, and a low frequency current flows into the electrode 5e to perform a curing. Therefore, a nonexpert or amateur can easily perform a low frequency curing. The switching circuit 27 alternately switches the electrodes 5e where a low frequency current flows (S22, S23), and habituation of an acupuncture point can be avoided and the curing effect can be maintained. Furthermore, since an acupuncture point region is detected repeatedly for every specific time (S24: Yes, S21), an effective curing can be done by tracing a spot where a curing is needed.

Moreover, in the third embodiment, a low frequency current is made to flow into only one electrode 5e for one time; however, it may be designed to flow into a plurality of electrodes 5e for one time. In step S21, after all the electrodes 5e are checked on the electric conductivity, an electrode 5e giving the highest electric conductivity is detected among them. However, the curing process may be arranged such that a standard electric conductivity is stored beforehand in the optimum electrode discriminating circuit 24, the electric conductivity of an electrode 5e is compared with the standard electric conductivity every time the discriminating circuit 24 measures one, and if the difference between the standard and the measured conductivity is within the specified range, the electrode 5e is judged as an electrode attached inside the acupuncture point region. This will speed up the electrode detection process of step S21 (compared with the case that electric conductivities are measured in all the electrodes 5e).

Figure 8A:
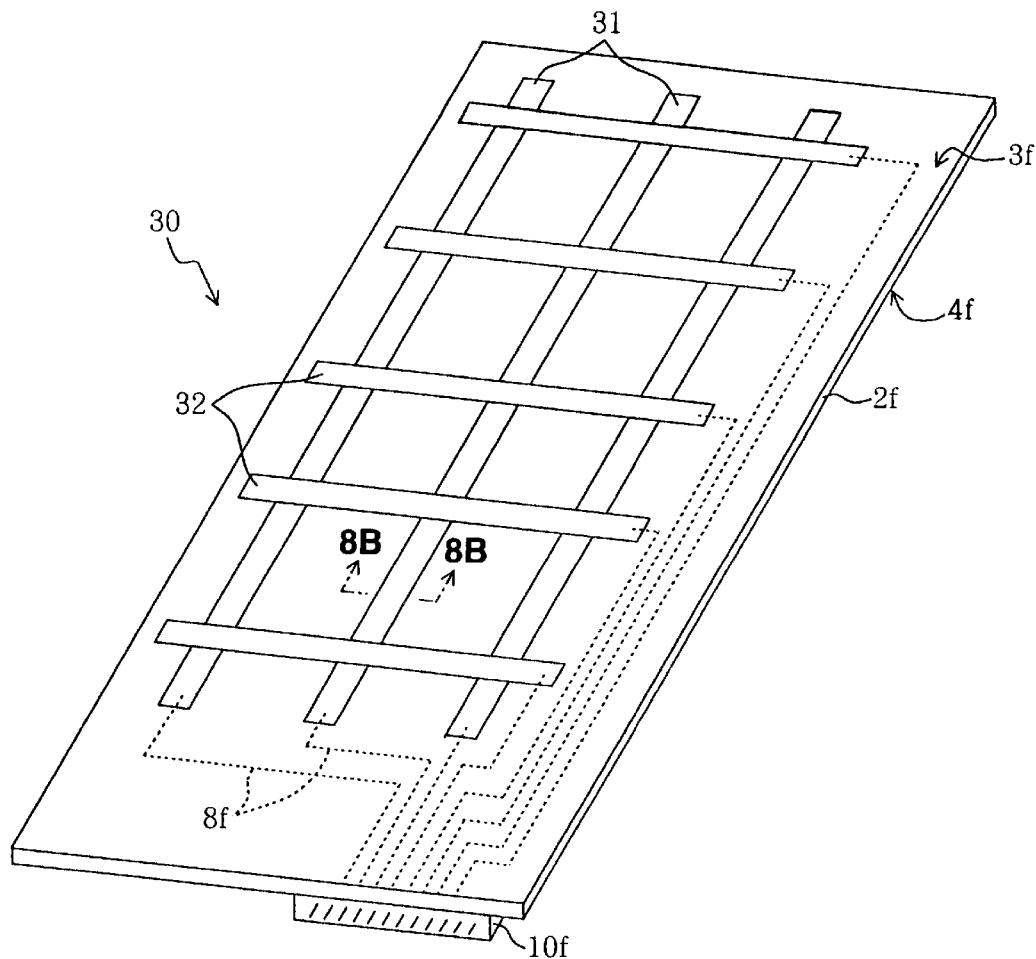
FIG. 8A is a schematic perspective view of a low frequency curing unit in the fourth embodiment.
Figure 8B:
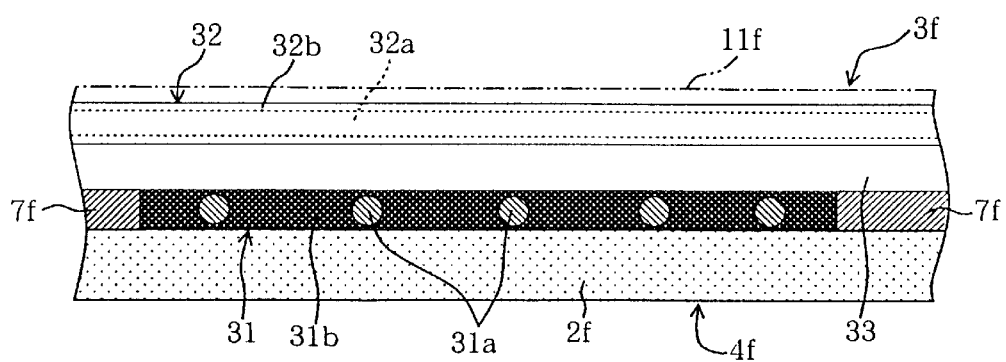
FIG. 8B is a side section taken along the line B—B in FIG. 8A.

Next, the fourth embodiment will be described with reference to FIGS. 8A and 8B. FIG. 8A is a schematic perspective view of a low frequency curing electrode assembly 30 in the fourth embodiment, and FIG. 8B is a side section taken along the line B—B in FIG. 8A. The fourth embodiment is constructed by modifying the low frequency curing electrode assembly 21 of the low frequency curing unit 60 in the third embodiment. The low frequency current generator connected to the low frequency curing electrode assembly 30 of the fourth embodiment is identical to that of the third embodiment, and the description will be omitted. The parts composed of members identical to the first embodiment, of the low frequency curing electrode assembly 30 of the fourth embodiment, are given the same number with appended reference letter "f", and a repetitive description will be omitted.

As shown in FIG. 8A, the low frequency curing electrode assembly 30 is provided with strips of tape of electrodes 31 and 32 arrayed in a grid-form on a rectangular base material 2f. As shown in FIG. 8B, the electrodes 31, 32 are composed of a plurality of long thin conductors 31a, 32a and conductive pastes 31b, 32b covering the long thin conductors 31a, 32a. A base material 33 having flexibility and insulating capability is interposed between the electrodes 31 and 32 as seen from the cross section. The base material 33 has a similar shape to the electrode 32 disposed thereabove and is formed in a strip of tape having a slightly large size. The electrode 32 is formed so as to run along on the base material 33. Since the electrode 32 is disposed on the base material 33 and the electrode 31 is disposed under the base material 33, each of the electrodes 31, 32 is isolated by the base material 33. The space between the electrodes 31 and 32 is designed to be minute to the extent that both electrodes do not electrically come into contact.

According to the low frequency curing electrode assembly 30 of the fourth embodiment, since the electrodes 31, 32 are formed in a strip of tape, the curing can be done over a wide area such as a subject's entire waist or entire shoulder. Since the base materials 2f, 33 and the electrodes 31, 32 have flexibility, the low frequency curing electrode assembly 30 can be conformed to the body.

The present invention has been described on the basis of the embodiments as above, however, the present invention is not at all limited to the aforementioned embodiments, and it is easily conceived that numerous modifications and changes can be made within the true spirit and scope of the invention.

For example, it is possible that the electrocardiographic electrode assembly 1 of the first embodiment is connected to the low frequency current generator 23 to use it as the low frequency curing electrode assembly. Conversely, the low frequency curing electrode assembly 21 of the third embodiment is connected to the electrocardiograph 15 to use it as the electrocardiographic electrode assembly. Furthermore, the electrode assemblies 1, 21, 30 of the respective embodiments can be used not only for the electrocardiographic measurement or low frequency curing, but also for other applications, for example, an electrode assembly for measurement of a blood glucose level, an electrode assembly for measurement of a body temperature, an electrode assembly for a brain wave measurement, and a sensing electrode assembly in an apnea syndrome sensor.

In the foregoing embodiments, the electrocardiograph 15 or the low frequency current generator 23 is connected to the electrode assembly 1, 21, or 30 through the cable 9, 17, or 17e. However, it may be conceivable that the measurement unit/curing unit of the electrocardiograph 15/low frequency current generator 23 is miniaturized to be incorporated in each of the electrode assemblies 1, 21, and 30. This construction will eliminate the cable connecting an electrode assembly to a measurement or curing unit while enhancing the portability to enable 24 hour-continuous attachment of the equipment.

What is claimed is:

1. A medical device comprising:
    a medical electrode assembly attachable to a human body and including a plurality of electrically isolated electrodes; and
    a measuring unit connected to the medical electrode assembly, the measuring unit including:
        an electrode detector coupled with each of the plurality of electrodes, the electrode detector discriminating a suitable electrode for measurement among the plurality of electrodes, wherein the electrode detector comprises structure that stores standard data relating to an optimum result, performs test measurements of each of the plurality of electrodes when detecting the suitable electrode, compares test measurement results with the standard data, and discriminates the suitable electrode by selecting an electrode that deviates the least from the standard data as the suitable electrode, and
        a storage device communicating with the electrode detector, the storage device storing a measurement result in accordance with data from the suitable electrode.

2. A medical device as claimed in claim 1, wherein the electrode detector comprises an indicator that indicates when the suitable electrode has been detected.

3. A medical device as claimed in claim 1, wherein the electrode detector comprises an indicator that indicates that the suitable electrode cannot be detected when the difference between the test measurement results of each of the electrodes and the sample data is not within a specified range.

4. A medical device as claimed in claim 3, wherein the indicator comprises one of a buzzer, lighting by an LED, display by a CRT or LCD that the suitable electrode cannot be detected.

5. A medical device as claimed in claim 1, wherein when the electrode detector compares the sample data with the test measurement results every time the test measurement is performed for one of the electrodes and the difference is within a specified range, the electrode detector selects the one electrode as the suitable electrode.

6. A medical device as claimed in claim 1, wherein the electrode detector comprises structure that performs detection of the suitable electrode repeatedly over predetermined time intervals, and the suitable electrode is changed based on the detection result.

7. A medical device as claimed in claim 1, further comprising an electrode detection switch coupled with the electrode detector, the electrode detector detecting the suitable electrode every time the electrode detection switch is operated.

8. A medical device as claimed in claim 1, further comprising a sensor coupled with the electrode detector, the sensor sensing a change of electrostatic capacity of the medical electrode assembly, wherein when the sensor detects a change of electrostatic capacity, the electrode detector detects the suitable electrode.

9. A medical device as claimed in claim 1, wherein the measuring unit is an electrocardiograph and the electrocardiograph is connected to the medical electrode assembly to form an electrocardiographic measurement unit.

10. A medical device as claimed in claim 1, wherein the medical electrode assembly and the measuring unit are self-contained in a single portable unit.

11. A medical device comprising:
    a medical electrode assembly attachable to a human body and including a plurality of electrically isolated electrodes; and
    a measuring unit connected to the medical electrode assembly, the measuring unit including:
        an electrode detector coupled with each of the plurality of electrodes, the electrode detector discriminating a suitable electrode for measurement among the plurality of electrodes and comprising structure that stores standard data relating to an optimum result, performs test measurements of the plurality of electrodes when detecting the suitable electrode, compares test measurement results with the standard data, and discriminates the suitable electrode, wherein when the difference between the test measurement results from a currently detecting electrode and the standard data is within a specified range, the electrode detector stops further detecting and discriminates the currently detecting electrode as the suitable electrode, and
        a storage device communicating with the electrode detector, the storage device storing a measurement result in accordance with data from the suitable electrode.

12. A medical device as claimed in claim 11, wherein the medical electrode assembly and the measuring unit are self-contained in a single portable unit.

13. A medical device as claimed in claim 11, wherein the electrode detector comprises an indicator that indicates when the suitable electrode has been detected.

14. A medical device as claimed in claim 11, wherein the electrode detector comprises an indicator that indicates that the suitable electrode cannot be detected when the difference between the test measurement results of each of the electrodes and the sample data is not within a specified range.

15. A medical device as claimed in claim 11, wherein the electrode detector comprises structure that performs detection of the suitable electrode repeatedly for every predetermined time internal, and the suitable electrode is changed based on the detection result.

16. A medical device as claimed in claim 11, further comprising an electrode detection switch coupled with the electrode detector, the electrode detector detecting the suitable electrode every time the electrode detection switch is operated.

17. A medical device as claimed in claim 11, further comprising a sensor coupled with the electrode detector, the sensor sensing a change of electrostatic capacity of the medical electrode assembly, wherein when the sensor detects a change of electrostatic capacity, the electrode detector detects the suitable electrode.

18. A medical device as claimed in claim 11, wherein the measuring unit is an electrocardiograph and the electrocardiograph is connected to the medical electrode assembly to form an electrocardiographic measurement unit.

19. A medical device comprising:
   a medical electrode assembly attachable to a human body and including a plurality of electrically isolated electrodes; and
   a curing unit formed of a low frequency current generator connected to the medical electrode assembly, the curing unit including:
      an electrode detector coupled with each of the plurality of electrodes, the electrode detector discriminating a suitable electrode for curing among the plurality of electrodes repeatedly over a predetermined time interval, and
      a curing device communicating with the electrode detector, the curing device performing a curing operation with the suitable electrode and flowing a low frequency current to the suitable electrode in accordance with output from the electrode detector, wherein the curing device flows a low frequency current alternately into the suitable electrode and an electrode adjacent the suitable electrode to perform a low frequency curing.

20. A medical device as claimed in claim 19, wherein the medical electrode assembly and the curing unit are self-contained in a single portable unit.

21. A method of operating a medical device including a medical electrode assembly having a plurality of electrically isolated electrodes and a measuring unit having an electrode detector and a storage device, the method comprising:
   (a) discriminating, with the electrode detector, a suitable electrode for measurement among the plurality of electrodes, the discriminating step including:
      (a1) performing test measurements of each of the plurality of electrodes;
      (a2) comparing test measurement results with standard data; and
      (a3) discriminating the suitable electrode based on results of step (a2) by selecting an electrode that outputs a measurement that deviates the least from the standard data as the suitable electrode; and
   (b) storing, in the storage device, a measurement result in accordance with data from the suitable electrode.

22. A medical device comprising:
   a medical electrode assembly attachable to a human body and including a plurality of electrically isolated electrodes; and
   a curing unit formed of a low frequency current generator connected to the medical electrode assembly, the curing unit including:
      an electrode detector coupled with each of the plurality of electrodes, the electrode detector discriminating a suitable electrode for curing among the plurality of electrodes repeatedly over a predetermined time interval, and
      a curing device communicating with the electrode detector, the curing device performing a curing operation with the suitable electrode and flowing a low frequency current to the suitable electrode in accordance with output from the electrode detector,
   wherein the plurality of electrodes are formed in a strip of tape and arrayed in a grid-form.

* * * * *